US010264958B2

(12) United States Patent
McWilliam et al.

(10) Patent No.: US 10,264,958 B2
(45) Date of Patent: Apr. 23, 2019

(54) SENSOR-EQUIPPED LARYNGOSCOPE AND SYSTEM AND METHOD FOR QUANTIFYING INTUBATION PERFORMANCE

(71) Applicant: UNIVERSITY OF NEW HAMPSHIRE, Durham, NH (US)

(72) Inventors: Paula L. McWilliam, Durham, NH (US); Brian J. King, Nottingham, NH (US); Mark Scott Granoff, Auburn, NH (US); Louis Patrick Halamek, Palo Alto, CA (US)

(73) Assignees: University of New Hampshire, Durham, NH (US); The Board of Trustees of the Leland Stanford Junior University, Stanford, CA (US)

( * ) Notice: Subject to any disclaimer, the term of this patent is extended or adjusted under 35 U.S.C. 154(b) by 314 days.

(21) Appl. No.: 15/297,869

(22) Filed: Oct. 19, 2016

(65) Prior Publication Data
US 2017/0105614 A1    Apr. 20, 2017

Related U.S. Application Data

(60) Provisional application No. 62/243,456, filed on Oct. 19, 2015.

(51) Int. Cl.
*A61B 1/267* (2006.01)
*A61B 1/00* (2006.01)
(Continued)

(52) U.S. Cl.
CPC .......... *A61B 1/267* (2013.01); *A61B 1/00016* (2013.01); *A61B 1/00032* (2013.01);
(Continued)

(58) Field of Classification Search
CPC . A61B 1/267; A61B 1/00016; A61B 1/00018; A61B 1/00032; A61B 1/00045;
(Continued)

(56) References Cited

U.S. PATENT DOCUMENTS 6,123,666 A * 9/2000 Wrenn ...................... A61B 1/05
434/262
2003/0088156 A1 * 5/2003 Berci ................. A61B 1/00188
600/188

(Continued)

FOREIGN PATENT DOCUMENTS

CN    202859071 U    4/2013
WO    2014109659 A1    7/2014

OTHER PUBLICATIONS

PCT International Preliminary Report on Patentability dated May 3, 2018, received in corresponding PCT Application No. PCT/US16/57720, 7 pgs.

(Continued)

*Primary Examiner* — Samchuan C Yao
*Assistant Examiner* — Michael Humphrey
(74) *Attorney, Agent, or Firm* — Grossman, Tucker, Perreault & Pfleger, PLLC

(57) ABSTRACT

A sensor-equipped laryngoscope may be used in a system and method for quantifying intubation performance. The level of experience of health care professionals (HCPs) plays a role in the application of force and torque applied to the laryngoscope during endotracheal intubation on an airway simulator, such as a manikin or animal model (e.g., a ferret). A sensor-equipped laryngoscope may provide data that differentiates the mechanics applied by subject matter experts (SMEs) (e.g., neonatologists) from those by novices or trainees during intubation, particularly on infant or neonatal airway simulators. A laryngoscope may be equipped with one or more sensors (e.g., force/torque sensors, accel- (Continued)

erometers, and gyroscopes) to record force, torque, and/or three-dimensional motion during endotracheal intubation. The sensor-equipped laryngoscope may then be used to record intubation mechanics (e.g., during an infant airway simulated intubation) for both SMEs and trainees.

11 Claims, 10 Drawing Sheets

(51) Int. Cl.
    *A61M 16/04*     (2006.01)
    *G09B 5/02*     (2006.01)
    *G09B 23/28*     (2006.01)
    *A61B 5/00*     (2006.01)

(52) U.S. Cl.
    CPC ........ *A61B 1/00057* (2013.01); *A61B 5/0048* (2013.01); *A61M 16/0488* (2013.01); *G09B 5/02* (2013.01); *G09B 23/285* (2013.01); *A61M 2205/332* (2013.01); *A61M 2209/02* (2013.01)

(58) Field of Classification Search
    CPC ... A61B 1/00057; A61B 1/00066; A61B 1/05; A61B 1/06; A61M 16/0488; A61M 2205/332; A61M 2209/02; G09B 23/285; G09B 23/286; G09B 5/02
    See application file for complete search history.

(56) References Cited

U.S. PATENT DOCUMENTS

| | | | | |
|---|---|---|---|---|
| 2005/0244801 | A1* | 11/2005 | DeSalvo | A61B 1/267 434/262 |
| 2006/0232664 | A1* | 10/2006 | Toly | G09B 23/285 348/45 |
| 2007/0049794 | A1* | 3/2007 | Glassenberg | A61B 1/00032 600/109 |
| 2009/0114217 | A1* | 5/2009 | Wulfsohn | A61B 1/267 128/200.26 |
| 2010/0261968 | A1* | 10/2010 | Nearman | A61B 1/00041 600/188 |
| 2011/0010155 | A1* | 1/2011 | Takanishi | G09B 23/32 703/11 |
| 2011/0077466 | A1* | 3/2011 | Rosenthal | A61B 1/00045 600/188 |
| 2012/0124572 | A1* | 5/2012 | Cunningham | G06F 9/45558 718/1 |
| 2013/0197312 | A1* | 8/2013 | Miller | A61B 1/267 600/188 |
| 2013/0216992 | A1* | 8/2013 | Simeoni | G09B 23/285 434/265 |
| 2014/0160261 | A1* | 6/2014 | Miller | A61B 1/00052 348/77 |
| 2014/0343359 | A1* | 11/2014 | Farr | A61B 1/00052 600/109 |
| 2014/0370474 | A1* | 12/2014 | Thompson | A61B 1/00131 434/262 |
| 2015/0064675 | A1* | 3/2015 | Eichhorn | A61B 17/29 434/262 |
| 2015/0079565 | A1* | 3/2015 | Miller | G09B 23/281 434/252 |
| 2016/0015467 | A1* | 1/2016 | Vayser | G06N 5/02 600/245 |
| 2016/0051781 | A1* | 2/2016 | Isaacs | A61M 16/0488 600/188 |
| 2016/0058276 | A1* | 3/2016 | Ramos Da Silva | A61B 1/00034 600/196 |

OTHER PUBLICATIONS

ATI Industrial Automation, Multi-Axis Force/Torque Sensor, www.ati-ia.com, Jul. 23, 2014, 44 pp.

"MultiAxis Force/Torque Sensors", ATI Industrial Automation, Product page, Jun. 26, 2005, retrieved from internet on Dec. 12, 2016, URL: http://www.ati-ia.com/products/ft/sensors.aspx, paragraphs 1-2, 2 pgs.

PCT International Search Report and Written Opinion dated Feb. 22, 2017, received in corresponding PCT Application No. PCT/US16/57720, 9 pgs.

* cited by examiner

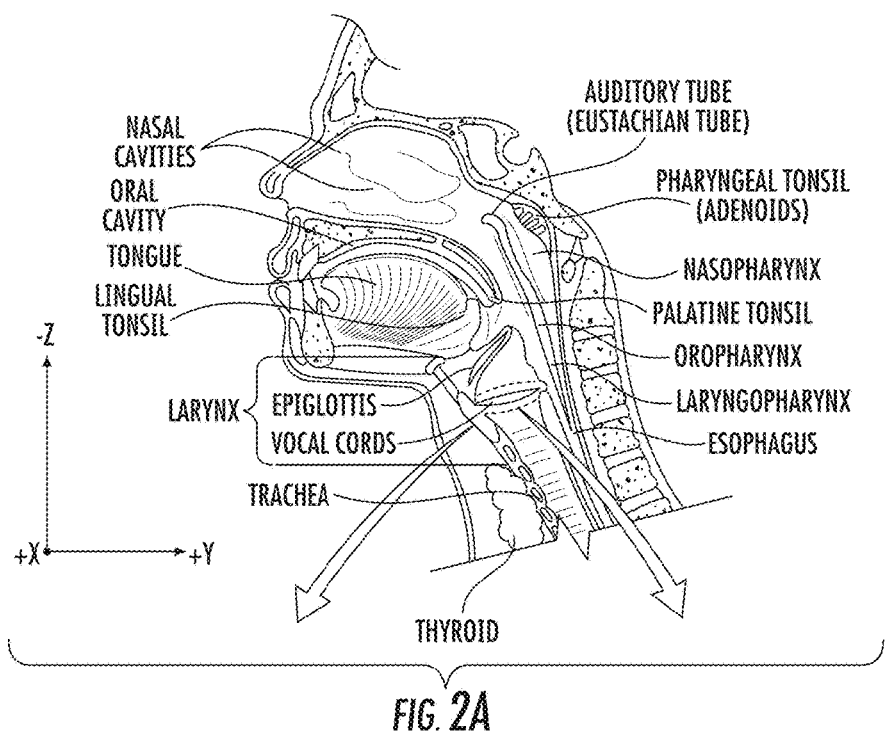
FIG. 2A
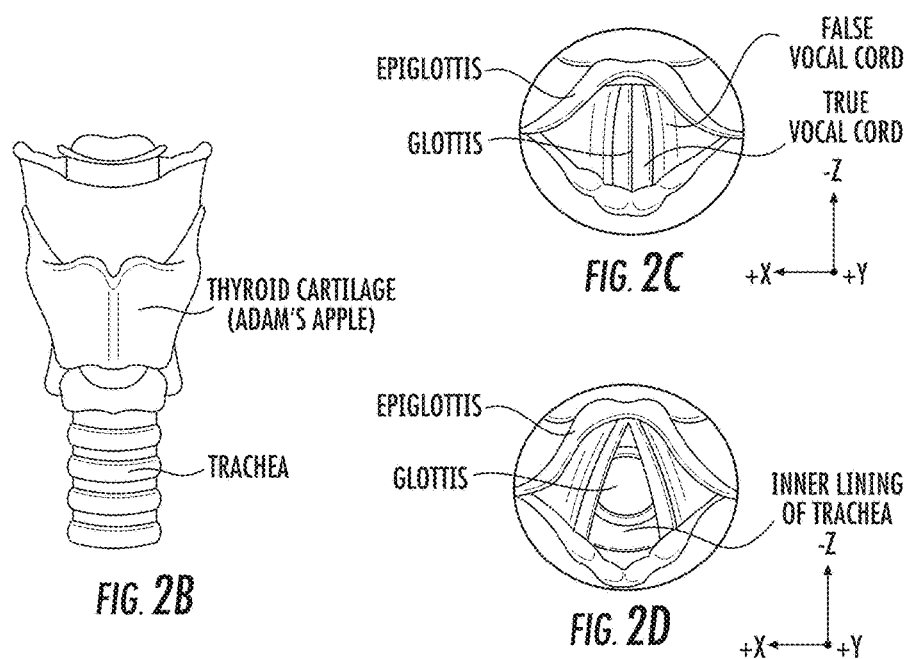
FIG. 2B
FIG. 2C
FIG. 2D

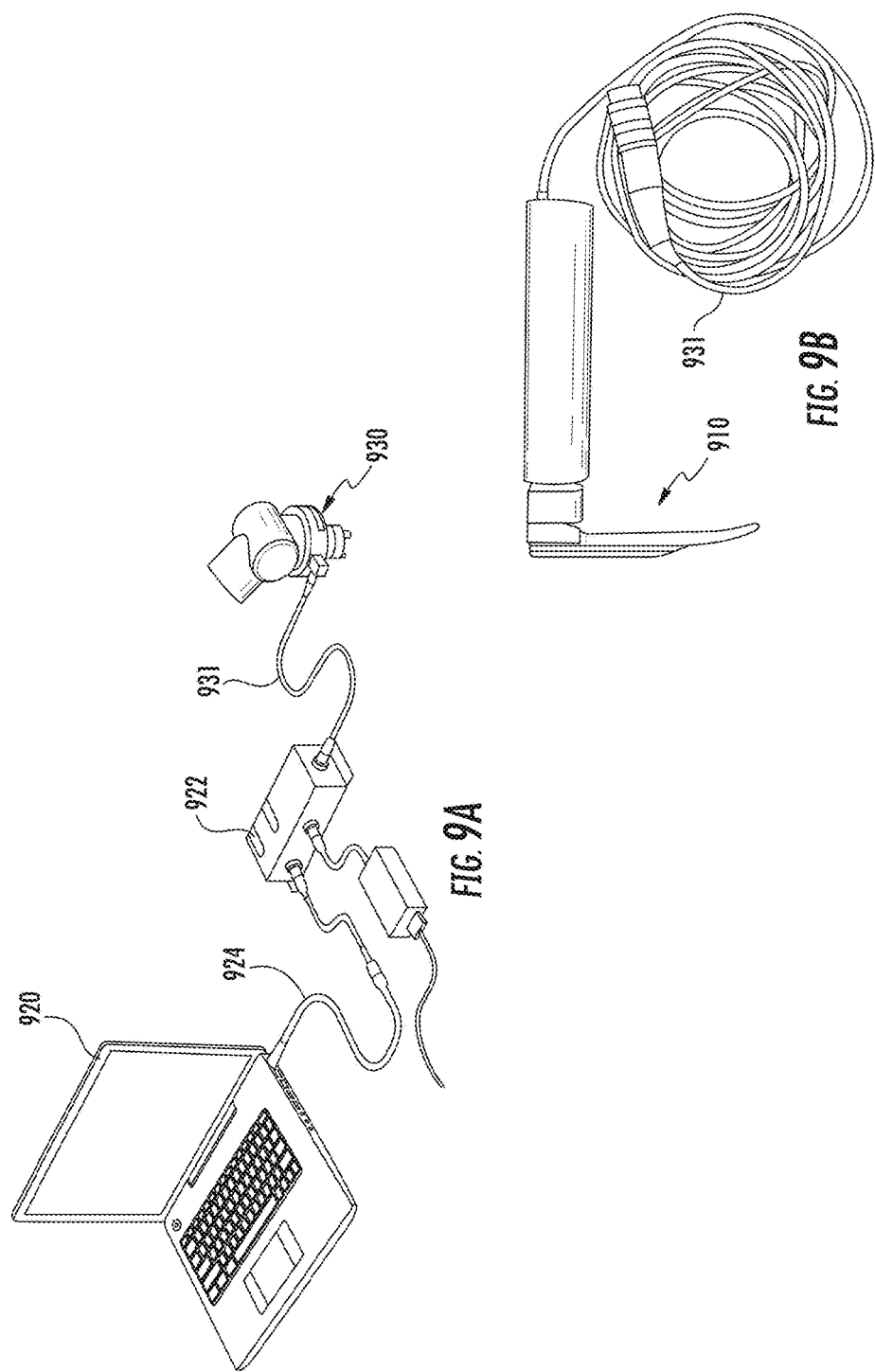

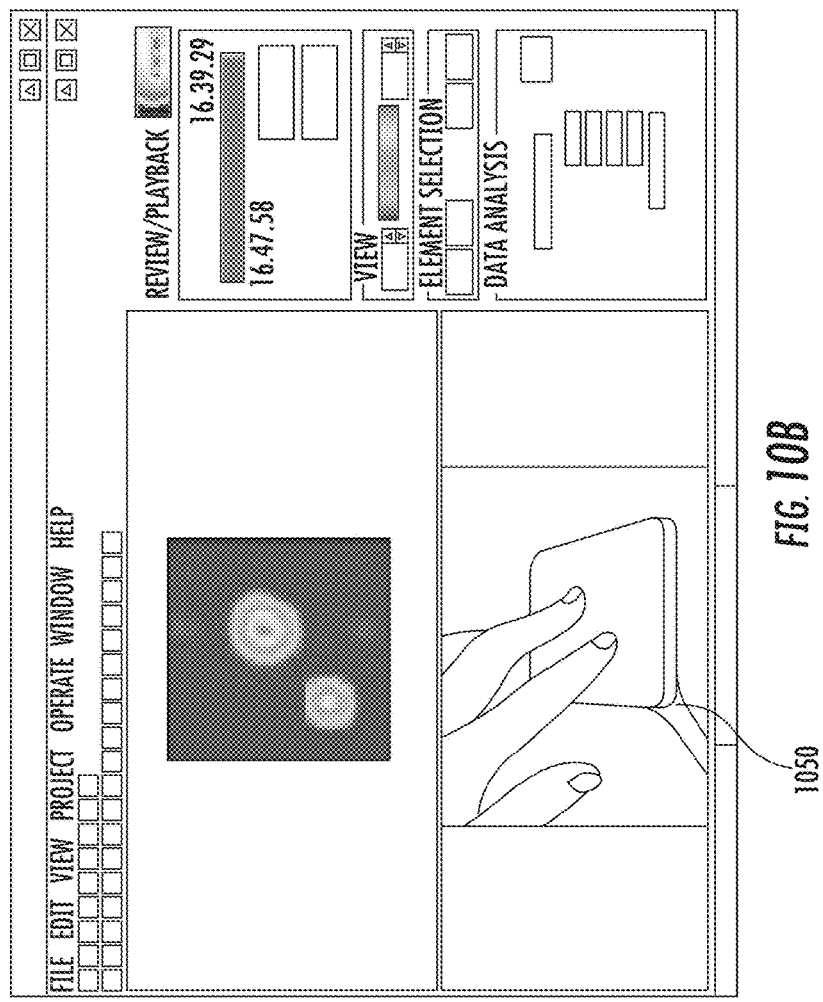
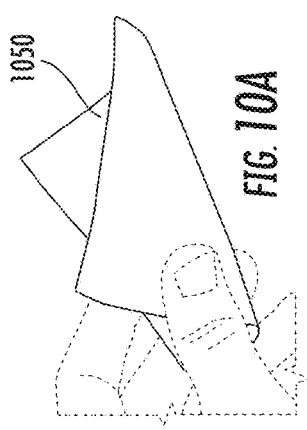
FIG. 10A
FIG. 10B

SENSOR-EQUIPPED LARYNGOSCOPE AND SYSTEM AND METHOD FOR QUANTIFYING INTUBATION PERFORMANCE

CROSS-REFERENCE TO RELATED APPLICATIONS

The present application claims the benefit of U.S. Provisional Patent Application Ser. No. 62/243,456 filed on Oct. 19, 2015, which is fully incorporated herein by reference.

TECHNICAL FIELD

The present disclosure relates to laryngoscopes and endotracheal intubation and more particularly, to a sensor-equipped laryngoscope and systems and methods for quantifying intubation performance using same.

BACKGROUND INFORMATION

Endotracheal intubation is a mandatory competency for many healthcare professionals (HCPs), such as physicians, neonatal nurse practitioners and respiratory therapists responsible for neonatal resuscitation. Neonatal intubation is a complex skill that requires critical procedural knowledge and experience. If the procedure is performed by an inexperienced HCP, life-threatening complications may arise. The American Academy of Pediatrics' (AAP) Neonatal Resuscitation Program (NRP) recommends a 30-second limit for intubation attempts, and studies have revealed that pediatric residents had a high failure rate of attempted intubation.

HCPs require training and practice to execute precise, controlled insertion of a laryngoscope to achieve successful endotracheal tube placement. HCP training involves rigorous and repetitive practice as they conduct intubation on actual patients sporadically and infrequently. Intubation training is often performed using plastic models or manikins that lack realistic anatomic features. Subject matter experts (SMEs), e.g., experienced physicians, have a failure rate of 0.1% while less experienced HCPs, such as residents, have failure rates of 25-33%. Failure to use the laryngoscope effectively may lead to damage of soft tissues (e.g., the larynx or esophagus) or result in life-threatening changes in heart rate and/or blood pressure. Training may be hindered by the lack of realistic simulators and quantitative tools to evaluate the necessary competency for successful airway intervention.

In the United States and Canada, endotracheal intubation is initially taught to all trainees through participation in the AAP'S NRP. NRP provides a standardized approach to the technical aspects of neonatal resuscitation, which includes the intervention of endotracheal intubation. This approach to learning the neonatal intubation procedure consists of a review of literature, didactic instruction, skills training using patient simulators and observation of the intervention as performed by a more experienced colleague at the bedside. The trainees then perform the actual technical procedure on patients under the supervision of senior colleagues.

Furthermore, the successful completion of NRP does not ensure that HCPs have acquired the necessary competence to perform neonatal resuscitation. Clinical supervision is required for HCPs to assume responsibility for any portion of neonatal resuscitation including the intervention of intubation. This creates a significant challenge for trainees, such as pediatric residents, to become competent in the intervention of neonatal intubation because the current guidelines of the Accreditation Council for Graduate Medical Education (ACGME) and the Residency Review Committee (RRC) for Pediatrics have restricted the amount of intensive care experience obtained during pediatric residency. These training guidelines state that the neonatal intensive care curricula must be structured to train residents to perform delivery room resuscitation and stabilization of infants.

Residents are expected to learn procedural skills applicable to general pediatrics including endotracheal intubation. Although the ACGME requires competence in endotracheal intubation as part of the pediatric residency training, no definition for procedural competence is outlined in the common program requirements. In addition, these training guidelines specify that experience should be graduated so that residents build and maintain skills throughout their training program. However, the training guidelines limit the residents' experience and exposure to neonatal resuscitation by restricting neonatal and pediatric intensive care rotations to a maximum of six months. Given these restrictions, residents complete training with a small number of hands-on experiences in neonatal intubation. Consequently, simulation-based training for acquiring neonatal intubation skills may offer greater opportunity than 'real-life' clinical experiences for teaching, learning and refinement of relevant knowledge and development of skills.

The methods of training HCPs have changed and it is no longer acceptable to practice intubation technique on infants who have died. Other training models of intubation have included animals and patient simulators. With technological advancements, high fidelity manikin-based simulators are most commonly used in neonatal resuscitation training programs to provide a risk-free environment for trainees to develop procedural skills and decision-making under highly controlled circumstances. NRP instructors present case scenarios that create environmental fidelity as would be experienced in the delivery room. However, neonatal patient simulators lack the cues necessary to engender realistic responses on the part of the HCPs using them.

All simulators have limitations in replication of physiology and anatomical variability. Although existing simulation-based training outcomes have been shown to provide trainees with increased confidence in treating neonates with acute physiologic changes, this confidence and/or perceived skill set may not translate to improved clinical practice. As such, knowledge is not necessarily transferred adequately into clinical practice using the currently available simulation methodologies and technologies.

Although successful neonatal endotracheal intubation is highly dependent on the HCP's technique, existing training methods and technologies have not provided quantitative evaluation of the mechanics (e.g., force and torque) of successful neonatal intubation. The forces exerted on the airway of a neonatal patient simulator are unlikely to reflect those of a safe and effective intubation of a real human neonatal patient. Training devices in use today do not provide sufficient feedback to trainees regarding the force they use during neonatal/infant intubation. As a result, training to a set of objective, quantitative standards for intubation mechanics is not part of existing curriculum for HCPs who perform this procedure. Because assessment of these skills is highly subjective (i.e., based on the opinion of an instructor), trainees may experience difficulty acquiring and maintaining the skills necessary for successful neonatal endotracheal intubation.

SUMMARY

Consistent with an embodiment, a sensor-equipped laryngoscope includes a blade portion configured to be inserted into a mouth and airway of a patient. A handle portion is coupled to the blade portion and includes at least one sensor. The sensor is mechanically coupled to the blade portion such that the sensor is responsive to forces applied to the blade portion for measuring the forces applied to the blade portion.

Consistent with another embodiment, a system is provided for quantifying intubation performance. The system includes a sensor-equipped laryngoscope configured to perform an intubation and configured to sense and measure intubation mechanics. The system also includes a data acquisition system configured to acquire and record intubation mechanics data from the sensor-equipped laryngoscope. The intubation mechanics data represent the intubation mechanics.

Consistent with a further embodiment, a method is provided for quantifying intubation performance. The method includes: measuring and recording a first set of intubation mechanics data representing intubation mechanics for a first group of subject matter experts SME; measuring and recording a second set of intubation mechanics data representing intubation mechanics for a second group of trainees; and comparing the first and second sets of intubation mechanics data.

BRIEF DESCRIPTION OF THE DRAWINGS

These and other features and advantages will be better understood by reading the following detailed description, taken together with the drawings wherein:

FIG. 2 is an illustration of a human airway region in which a sensor-equipped laryngoscope may be used, consistent with an embodiment of the present disclosure.

FIG. 9A is a photograph illustrating a system for quantifying intubation performance, consistent with an embodiment of the present disclosure.

FIG. 9B is a photograph illustrating a sensor-equipped laryngoscope for use in the system for quantifying intubation performance, consistent with an embodiment of the present disclosure.

FIGS. 10A-10D are illustrations of a system and method for quantifying intubation performance, consistent with another embodiment of the present disclosure.

DETAILED DESCRIPTION

Figure 1:
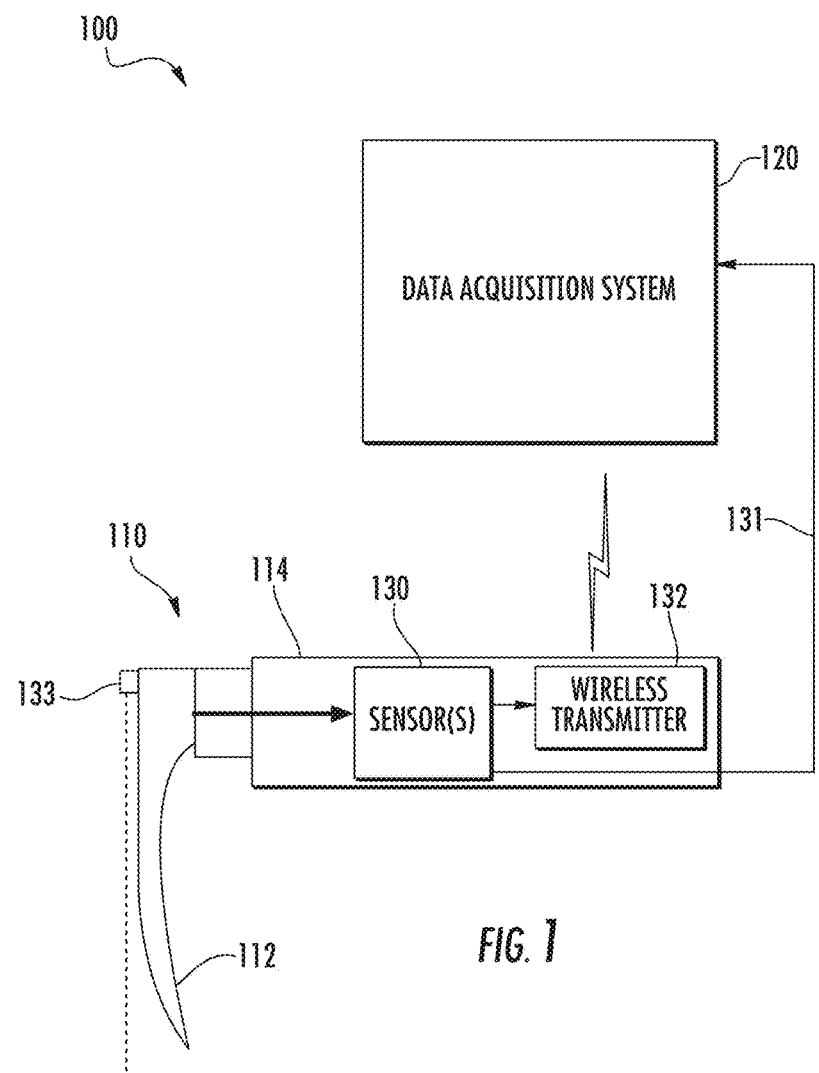
FIG. 1 is a diagrammatic view of a system for quantifying intubation performance, consistent with an embodiment of the present disclosure.

A sensor-equipped (or sensor-integrated) laryngoscope, consistent with embodiments of the present disclosure, may be used in a system and method for quantifying intubation performance. The level of experience of health care professionals (HCPs) plays a role in the application of force and torque applied to the laryngoscope during endotracheal intubation on an airway simulator, such as a manikin or animal model (e.g., a ferret). A sensor-equipped laryngoscope may provide data that differentiates the mechanics applied by subject matter experts (SMEs) (e.g., neonatologists) from those by novices or trainees during intubation, particularly on infant or neonatal airway simulators. A laryngoscope may be equipped with one or more sensors (e.g., force/torque sensors, accelerometers, and gyroscopes) to record force, torque, and/or three-dimensional motion during endotracheal intubation. The sensor-equipped laryngoscope may then be used to record intubation mechanics (e.g., during an infant airway simulated intubation) for both SMEs and trainees.

The device and system, consistent with embodiments of the present disclosure, may thus measure, acquire and store intubation mechanics data including force and torque on the laryngoscope blade as well as motion or kinematics of the blade (e.g., position, velocity, acceleration, and orientation) during endotracheal intubation. The system may also be designed to provide a haptic interface with a virtual simulation apparatus and may be hard wired or wireless. The system and method allows the HCP to verify standard procedures and protocols by comparing the recorded intubation mechanics. The device, system, and method can be modified for neonatal, pediatric and adult intubation.

The system and method for quantifying intubation performance, consistent with embodiments of the present disclosure, may provide baseline data that can be used to develop a path toward a simulator that will provide "real-time" multimodal feedback to trainees during neonatal, pediatric and adult intubation. The goal of simulation training methodologies is to present trainees with a highly realistic scenario while allowing for error and self-reflection. Although simulation-based training in healthcare has proven environmental fidelity, trainees feedback specific to "real-life" replication of the manikins used during simulation scenarios are consistently rated poorly. Effective simulation models such as augmented-virtual reality simulators with haptic force feedback can reduce the extended time required for inexperienced practitioners to practice skills such as neonatal intubation, reduce costly medical errors (requiring corrective interventions and compensation claims), and improve patient outcomes. An augmented-virtual reality simulator with haptic force feedback capabilities may remedy many of the deficiencies associated with manikin training technology. Trainees' accomplishments will be proven, rather than hoped-for, and will ultimately lead to higher quality patient outcomes.

Referring to FIG. 1, a system 100 for quantifying intubation performance, consistent with embodiments of the present disclosure, is shown and described. The system 100 generally includes a sensor-equipped laryngoscope 110 in communication with a data acquisition system 120. The sensor-equipped laryngoscope 110 includes a laryngoscope blade 112 coupled to a handle 114. The handle 114 contains at least one or more sensors 130 responsive to forces on and/or movement of the laryngoscope blade 112. The sensor-equipped laryngoscope 110 may thus be used to sense and measure intubation mechanics, for example, by sensing and measuring at least force and torque on the laryngoscope blade 112. The sensor-equipped laryngoscope 110 may also include a microcamera 133 located, for example, on or in the laryngoscope blade 112 to provide anatomical viewing while someone is performing an intubation. The sensor-equipped laryngoscope 110 may be used as an educational tool, for example, allowing instructors and other observers to watch during the intubation.

The sensor-equipped laryngoscope 110 may be coupled to the data acquisition system 120 with a wireless connection and/or a wired connection. To provide a wired connection, a cable 131 may extend from the sensor(s) 130 through a back end of the handle 114 to the data acquisition system 120. To provide a wireless connection, a wireless transmitter 132 may be located in the handle 114 and connected to the sensor(s) 132. The wireless transmitter 132 may be configured for any type of wireless communication including, without limitation, Bluetooth wireless communication and WiFi wireless communication.

The data acquisition system 120 may include a computer-based data acquisition system including a general purpose computer running data acquisition software, such as LabVIEW data acquisition software, for acquiring, displaying and storing the intubation mechanics data measured by the sensor(s) 130. The data acquisition software allows the basic display and analysis of the digitized sensor signals. The system 100 for quantifying intubation performance may also include other software, such as data analysis software for analyzing intubation data.

The system 100 for quantifying intubation performance may be used, for example, to measure force and torque relative to a coordinate system. FIG. 2 illustrates a coordinate system with X, Y and Z axes relative to the relevant regions around the mouth and airway of a patient. In this example, the Y axis runs generally along the oral cavity and the X and Z axes run generally perpendicular to the oral cavity.

Figure 3:
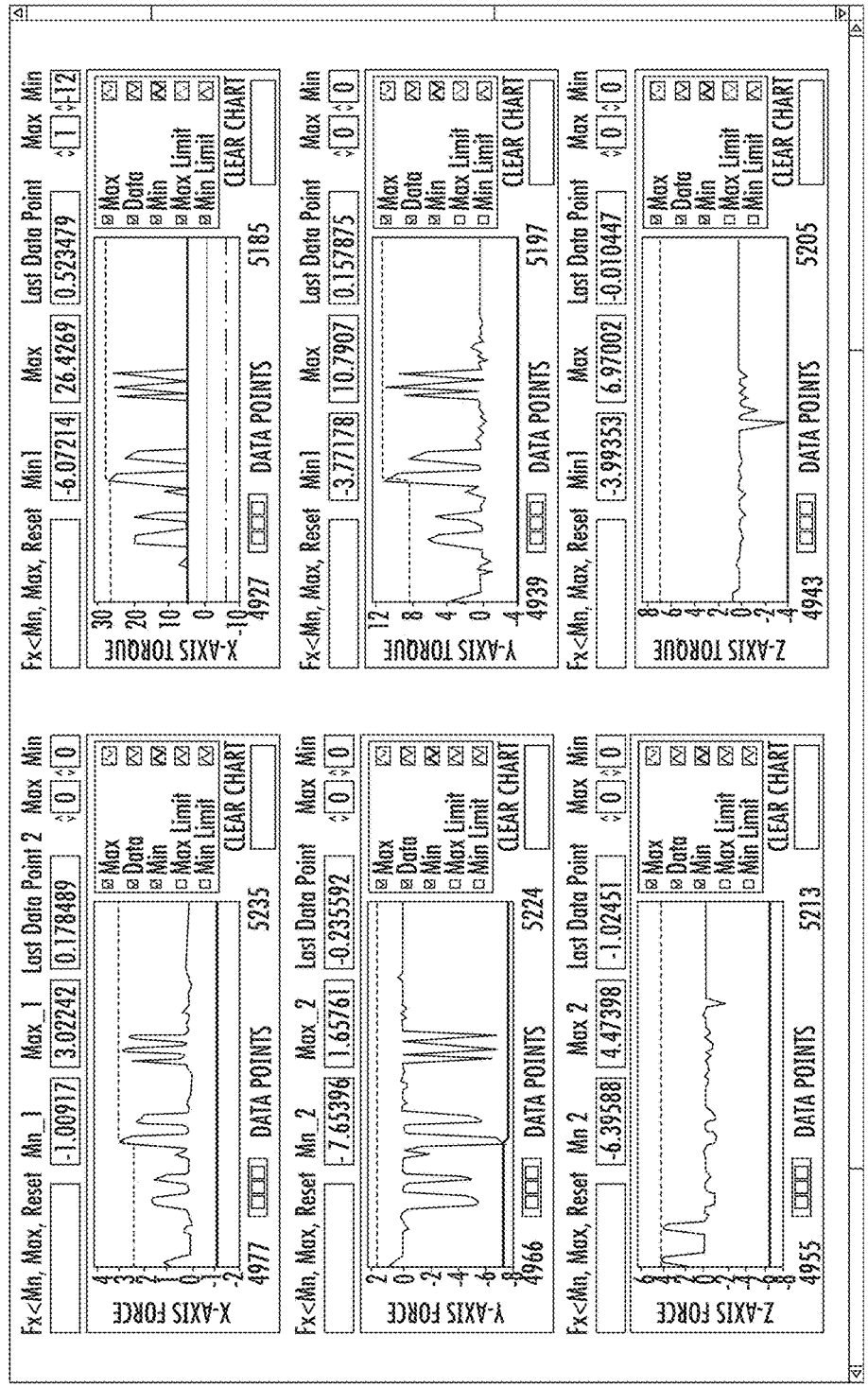
FIG. 3 is an illustration of a display of force and torque measurements obtained from a sensor-equipped laryngoscope, consistent with an embodiment of the present disclosure.

The data acquisition system 120 may be used to record and display the measured force and torque relative to the X, Y and Z axes. FIG. 3 illustrates a graphical display of the forces (e.g., in lbf) and torques (e.g., in lbf-in) on real time scroll charts. The real time scroll charts may include a file path and name where data is written to when selected and a stop (END) programming button. The scroll charts may display (e.g., at 7000 sample per second or every 147.7 μs) the real time force and torque in the X, Y and Z axes, the present or last data point, the minimum and maximum force and torque displacement in the X, Y and Z axes, and buttons that enable the ability to reset the minimum and maximum values and clear a chart. The plots to be shown (e.g., max, data, min, etc.) may be selected and/or deselected by checking boxes next to the data label. The charts may also have minimum and maximum limits or boundary conditions set to illustrate, in real time, when a force or torque has been exceeded. Other graphical displays of the measured data are also within the scope of the present disclosure.

Figure 4:
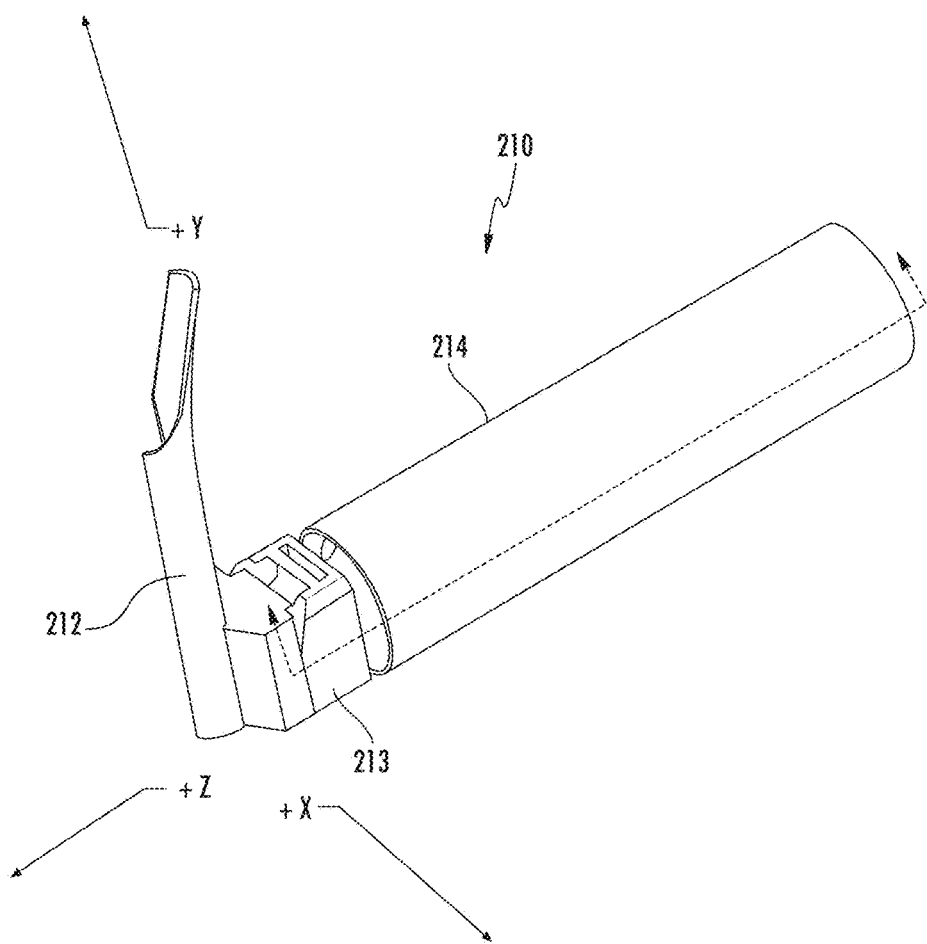
FIG. 4 is a perspective view of a sensor-equipped laryngoscope, consistent with an embodiment of the present disclosure.

Referring to FIG. 4, an embodiment of a sensor-equipped laryngoscope 210 is shown and described in greater detail. This embodiment of the sensor-equipped laryngoscope 210 is configured to sense and measure force and torque relative to the X, Y, and Z axes as shown. The sensor-equipped laryngoscope 210 includes a laryngoscope blade 212 coupled with a mechanical coupling 213 to a laryngoscope handle 214. The handle 214 encloses the sensor(s) and any supporting electronics for the sensors. The laryngoscope blade 212 is mechanically coupled to the one or more sensors located within the handle 214 such that the sensor(s) are responsive to forces and torques in the X, Y, and Z axes, as will be described in greater detail below. In this example, the X axis is substantially orthogonal to both the laryngoscope blade 212 and the handle 214, the Y axis runs substantially parallel to the laryngoscope blade 212, and the Z axis runs substantially parallel to the handle 214.

This embodiment of the sensor-equipped laryngoscope 210 may include eight transducers (strain gauges) built in to the handle 214. The sum of the signals from the transducers may be a measure of the axial thrust force and the differential signals may be a measure of the torque about an axis orthogonal to both the blade 212 and the handle axis at the end of the handle 214. The forces and torques on the blade 212 are transmitted to the transducers within the handle 214 of the laryngoscope 210.

Figure 5:
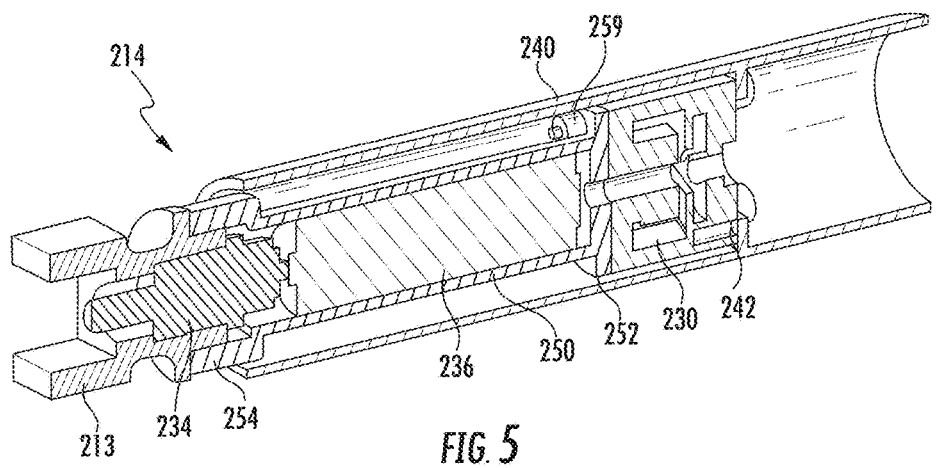
FIG. 5 is a cross-sectional view of an embodiment of the handle of the sensor-equipped laryngoscope shown in FIG. 4.

As shown in FIG. 5, the illustrated embodiment of the laryngoscope handle 214 includes a substantially cylindrical portion 240 enclosing a sensor 230 and a torque tube 250 for mechanically coupling the sensor 230 to the blade 212 via the mechanical coupling 213. In this embodiment, the laryngoscope handle 214 also includes a light source 234 and a battery 236 for powering at least the light source 234. One example of a light source 234 is a light emitting diode (LED), which provides visual enhancement by delivering a brighter light down the laryngoscope blade and allows for longer battery life. The battery 236 may also power the sensor 230 and other supporting electronics (e.g., a wireless transmitter) in a wireless configuration. Power may also be supplied via a cable (not shown) coupled through a back end of the handle 214. Other embodiments of the laryngoscope may not include a light source or battery.

Figure 6A:
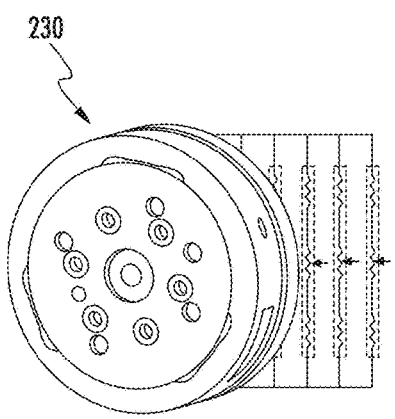
FIGS. 6A and 6B are perspective views of an embodiment of a force/torque transducer used in an embodiment of the sensor-equipped laryngoscope.
Figure 6B:
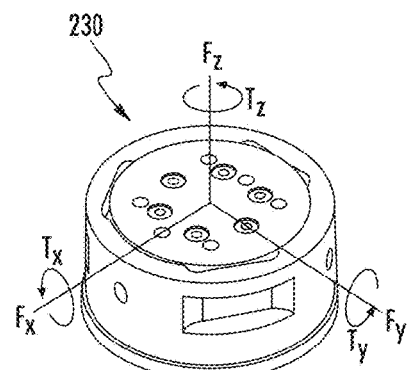
Figure 7A:
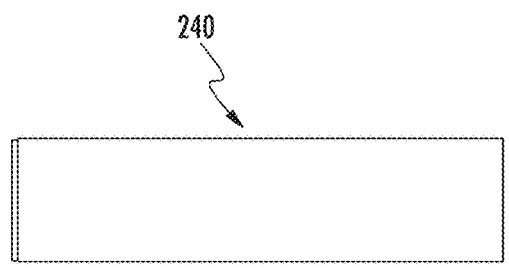
FIGS. 7A-7D are side, cross-sectional and end views of an embodiment of a cylindrical portion of a laryngoscope handle, consistent with an embodiment of the present disclosure.
Figure 7B:
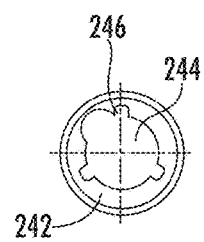
Figure 7C:
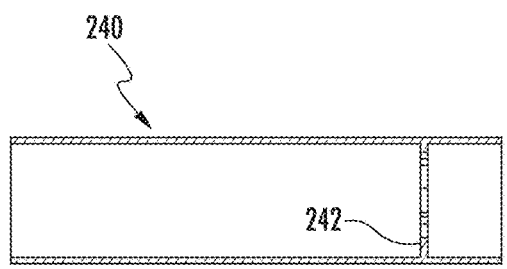
Figure 7D:
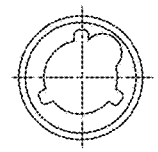
Figure 8A:
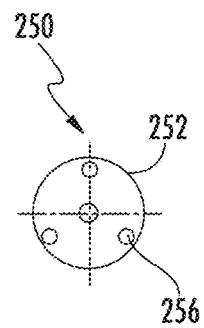
FIGS. 8A-8E are side, cross-sectional and end views of an embodiment of a torque tube used in a laryngoscope handle, consistent with an embodiment of the present disclosure.
Figure 8B:
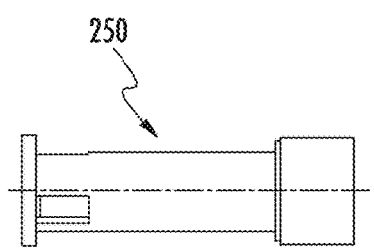
Figure 8C:
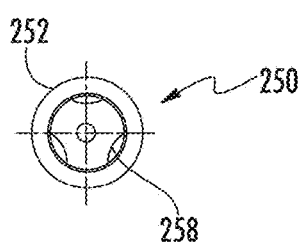
Figure 8D:
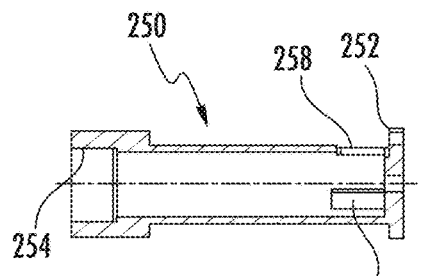
Figure 8E:
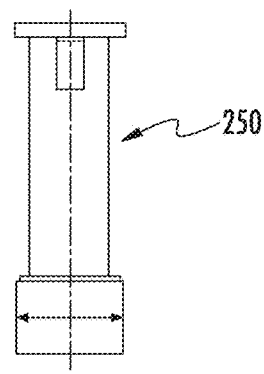
Figure 10C:
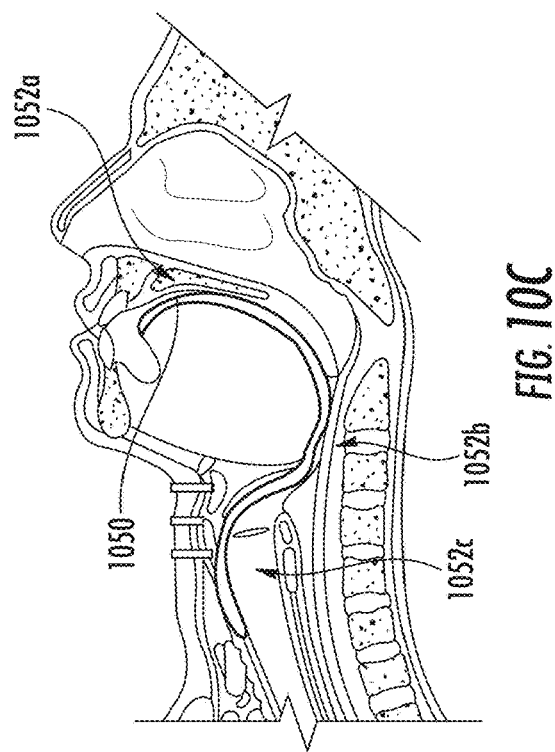
Figure 10D:
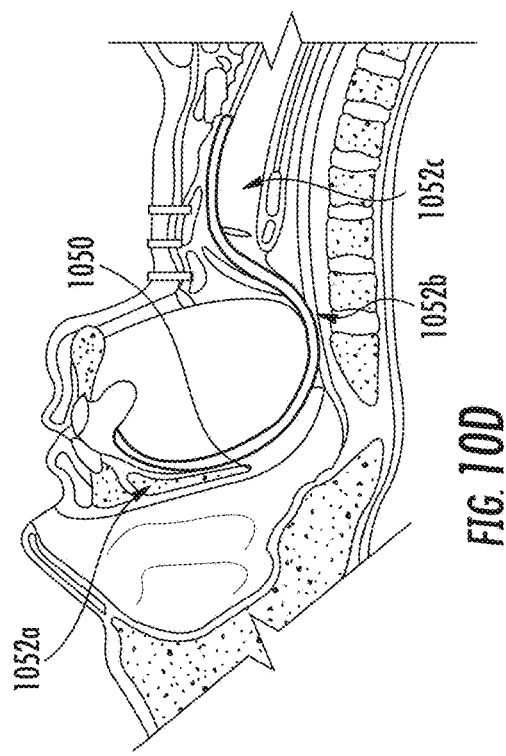

As shown in greater detail in FIGS. 6A and 6B, the sensor 230 may include a six-axis force/torque sensor or transducer such as the type available from ATI Industrial Automation. The six-axis force/torque sensor includes six independent sensors that together or differentially measure axial force and torque. The sensors may have a dynamic range sufficient to measure usually high forces, while providing sufficient precision for the forces and torques expected. The sensor 230 may thus be capable of sensing and recording data pertaining to the overall force and torque applied to the airway through the laryngoscope blade during intubation attempts. In other embodiments, the sensor-equipped laryngoscope may include any type of sensor or transducer capable of responding to force, torque, motion and/or any other parameter associated with intubation.

In one embodiment, the sensor-equipped laryngoscope 210 may be a modified version of a commercially available laryngoscope, such as a RUSCH® Fiberoptic Laryngoscope. In particular, the handle of the commercially available laryngoscope may be modified to accept the sensors and supporting electronics. The illustrated embodiment described herein includes only force and torque sensors to measure force and torque—two of the more important mechanics of intubation. Other embodiments may include, additionally or alternatively, sensors for measuring other mechanics of intubation such as position, velocity and orientation. These sensors may include, without limitation, accelerometers and gyroscopes.

As shown in greater detail in FIGS. 7A-7D, the cylindrical portion 240 includes a sensor seat 242 for seating the sensor 230 inside the handle 214. The sensor seat 242 may have a central aperture 244 and one or more cutaway portions 246 to allow a cable and/or fasteners to pass through. The sensor seat 242 may be located in the handle 214 such that the sensor 230 is seated proximate the midpoint of the handle 214. The handle 214 may thus be designed to accommodate the sensors while providing essentially the same form factor and center of gravity as a commercially available laryngoscope. Thus, the sensor-equipped laryngoscope mimics the balance of a standard laryngoscope. Although the illustrated embodiment shows a substantially cylindrical portion, other shapes are also within the scope of the present disclosure.

As shown in greater detail in FIGS. 8A-8D, the torque tube 250 includes a flange 252 at one end that is secured against the sensor 230 such that the torque tube 250 translates forces and torques in the three axes to the sensor 230. The torque tube 250 includes an internally threaded portion 254 at the opposite end for coupling to the coupling member 213. The torque tube 250 further includes holes 256 and access windows 258 to accommodate fasteners 259 (see FIG. 5) that secure the flange 252 to the sensor 230. Although the illustrated embodiment shows a torque tube for mechanically coupling the laryngoscope blade 212 with the sensor 230, other coupling mechanisms may also be used to allow the force and torque on the blade 212 to be sensed and recorded by a sensor in the handle 214.

The sensor-equipped laryngoscope 210 may also be designed to prevent damage to the sensor 230. For example, the laryngoscope 210 may be designed to prevent a user from collapsing the handle 214, which might damage the strain gauges. The laryngoscope 210 may also include other features to prevent over-stressing the sensors or transducers to protect the device from inadvertent excessive force or torque.

As shown in FIGS. 9A and 9B, an embodiment of a system 900 for quantifying intubation performance may include a sensor-equipped laryngoscope 910 and a computer 920 running data acquisition software. The sensor-equipped laryngoscope 910 includes a cable 931 that connects the sensor 930 inside the sensor-equipped laryngoscope 910 to a front-end electronics box 922. The electronics box 922 is connected to a power source and is connected to the computer 920 with a cable 924 such as a USB cable. Analog sensor signals from the sensor 930 are digitized (e.g., on a 100 ms cadence) in the front-end electronics box 922 and the digitized signals are delivered to the computer 920, for example, via the USB port. The data represented by the digitized signals may then be displayed and manipulated with the data acquisition software, for example, as described above.

As shown in FIGS. 10A-10D, another embodiment of a system for quantifying intubation performance may use pressure sensors inside a simulator such as a manikin. The pressure sensors may include, for example, pressure sensor pads 1050 such as a conformable TactArray sensor. The pressure sensors may be placed along the tongue, throat and esophagus regions 1052a, 1052b, 1052c. Contact points may then be mapped on a monitor displaying the right and left hand sides of a patient. This system may be used alone or together with a sensor-equipped laryngoscope as described above.

According to one method for obtaining data quantifying intubation performance, two groups of test subjects (i.e., a group of SMEs and a group of trainees) each perform intubations on simulators (e.g., infant airway simulators or animal models) using the sensor-equipped laryngoscope. The SMEs may be neonatologists skilled in infant intubation and the trainees may be pediatric residents undergoing intubation training. A subset of SMEs may be used to validate the data reproducibility from multiple intubation attempts. Time-tagged data and videos of these intubation attempts may be recorded and analyzed to determine if there are significant differences between the mechanics of intubation using test subject experience as the variable.

In one example, each test subject performs five successful intubations on an infant airway simulator such as a manikin or an animal model. A ferret may be suitable as the animal model because the upper respiratory tract approximates that of human neonates in physiologic appearance and size. A successful endotracheal intubation may be defined as correct placement of an endotracheal tube (ETT) into a trachea of a simulator within 30 seconds from the start of the procedure (i.e., when the laryngoscope blade enters the mouth). Correct placement of the ETT may be defined as insertion of the tube so that the vocal cord guide is at the level of the vocal cords, placing the tube at approximately halfway between the vocal cords and carina and auscultation of bilateral breath sounds. In order to auscultate bilateral breath sounds, a positive pressure device may be attached to the ETT, and the bilateral breath sounds may be auscultated while the ETT is held in place to assure that the ETT is in the correct placement.

The intubation forces, torque and/or motions are recorded and synchronized for each of the intubations with an accompanying video. The videos allow visualization of the phase of the intubation process corresponding to the data under study, which allows the numerical data captured by the sensors to be linked to the particular movements of the test subject during different phases of the intubation process. Where an animal model is used, the animal model may also be examined for airway trauma.

A paired t-test of the time-tagged data will be used to quantify differences in mechanics between the two groups of subjects. The quantified intubation mechanics data may then be compared between the two groups to identify the characteristics of successful intubations performed by SMEs, for example, the differences of forces and torques applied at different points during the intubation and the different movements. The intubation mechanics data and these identified characteristics may thus be used to provide an objective definition of competency in endotracheal intubation, precise methods of assessment of the intubation technique, and the development of rigorous, evidence-based training technologies and methodologies to facilitate the acquisition and maintenance of this important, life-saving skill. As such, the sensor-equipped laryngoscope and systems and methods for quantifying intubation performance described herein may improve the outcomes for newborns and serve as the basis for evaluation intubation in other patient populations.

Additionally or alternatively, a sensor-equipped laryngoscope may be used to perform intubations on live patients to collect data from human neonatal intubations, which may be used as a benchmark. A comparison of the data collected for a simulator and the data collected for a live patient may be used to suggest anatomical improvements in training simulators. Such data may also be used to develop safe yet effective limits of force and torque to be applied through the laryngoscope, for example, during neonatal and infant intubation.

Accordingly, the sensor-equipped laryngoscope and systems and methods described herein may be used to quantify intubation performance in a safe and controlled environment using manikins or animal models to collect comparative data for use in endotracheal intubation training and for use in improving laboratory simulators and training methodologies.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A sensor-equipped laryngoscope comprising:
a blade portion configured to be inserted into a mouth and airway of a patient; and
a handle portion coupled to the blade portion and including at least one sensor,
wherein the at least one sensor is seated within the handle; and
wherein the handle further includes an internal tube providing mechanical coupling between the at least one sensor and the blade portion;
wherein the at least one sensor is responsive to forces applied to the blade portion and translated by the internal tube for measuring the forces applied to the blade portion.

2. The sensor-equipped laryngoscope of claim 1, wherein the at least one sensor includes a force and torque sensor.

3. The sensor-equipped laryngoscope of claim 2 wherein the force and torque sensor includes a six-axis force and torque transducer.

4. The sensor-equipped laryngoscope of claim 1 wherein the handle portion further includes an accelerometer responsive to motion of the blade portion.

5. The sensor-equipped laryngoscope of claim 1 wherein the handle portion further includes a gyroscope responsive to motion of the blade portion.

6. The sensor-equipped laryngoscope of claim 1 wherein the handle portion further includes a wireless transmitter coupled to the at least one sensor for wirelessly transmitting sensor measurement signals.

7. The sensor-equipped laryngoscope of claim 1 further including a cable coupled to the at least one sensor for carrying sensor measurement signals.

8. The sensor-equipped laryngoscope of claim 1 wherein the handle further includes a battery.

9. The sensor-equipped laryngoscope of claim 1 wherein the handle further includes a light source.

10. The sensor-equipped laryngoscope of claim 1 further including a microcamera integrated into the blade portion for anatomical viewing during intubation.

11. The sensor-equipped laryngoscope of claim 1, wherein the at least one sensor is located proximate a midpoint of a longitudinal axis of the handle.

* * * * *